United States Patent [19]

McRae, Jr.

[11] Patent Number: 4,555,627
[45] Date of Patent: Nov. 26, 1985

[54] BACKSCATTER ABSORPTION GAS IMAGING SYSTEM

[75] Inventor: Thomas G. McRae, Jr., Livermore, Calif.

[73] Assignee: The United States of America as represented by the United States Department of Energy, Washington, D.C.

[21] Appl. No.: 482,380

[22] Filed: Apr. 5, 1983

[51] Int. Cl.[4] .......................................... G01N 21/35
[52] U.S. Cl. .................................. 250/334; 250/338; 250/330
[58] Field of Search ............... 250/341, 334, 330, 372, 250/339, 347, 338, 343; 358/113, 108

[56] References Cited

U.S. PATENT DOCUMENTS

| 3,032,655 | 5/1962 | Romans | 250/340 |
|---|---|---|---|
| 3,317,730 | 5/1967 | Hilsum . | |
| 3,517,190 | 6/1970 | Astheimer . | |
| 3,829,694 | 8/1974 | Goto | 250/339 |
| 3,832,548 | 8/1974 | Wallack | 250/343 |
| 4,204,121 | 5/1980 | Milly | 250/343 |
| 4,262,199 | 4/1981 | Bridges et al. | 250/347 |
| 4,264,209 | 4/1981 | Brewster | 250/343 |
| 4,303,862 | 12/1981 | Geiger | 250/372 |
| 4,347,530 | 8/1982 | Stetson | 250/347 |
| 4,390,785 | 6/1983 | Faulhaber et al. | 250/334 |
| 4,426,640 | 1/1984 | Becconsall et al. | 250/339 |
| 4,490,613 | 12/1984 | Brame | 250/341 |

OTHER PUBLICATIONS

Koopman et al., "Description and Analysis of Burro Series 40-m³ LNG Spill Experiments", UCRL-53186, Lawrence Livermore Lab., 8-14-81, 35 pages.

Primary Examiner—Alfred E. Smith
Assistant Examiner—Carolyn E. Fields
Attorney, Agent, or Firm—Henry P. Sartorio; L. E. Carnahan; Judson R. Hightower

[57] ABSTRACT

A video imaging system for detecting hazardous gas leaks. Visual displays of invisible gas clouds are produced by radiation augmentation of the field of view of an imaging device by radiation corresponding to an absorption line of the gas to be detected. The field of view of an imager is irradiated by a laser. The imager receives both backscattered laser light and background radiation. When a detectable gas is present, the backscattered laser light is highly attenuated, producing a region of contrast or shadow on the image. A flying spot imaging system is utilized to synchronously irradiate and scan the area to lower laser power requirements. The imager signal is processed to produce a video display.

17 Claims, 10 Drawing Figures

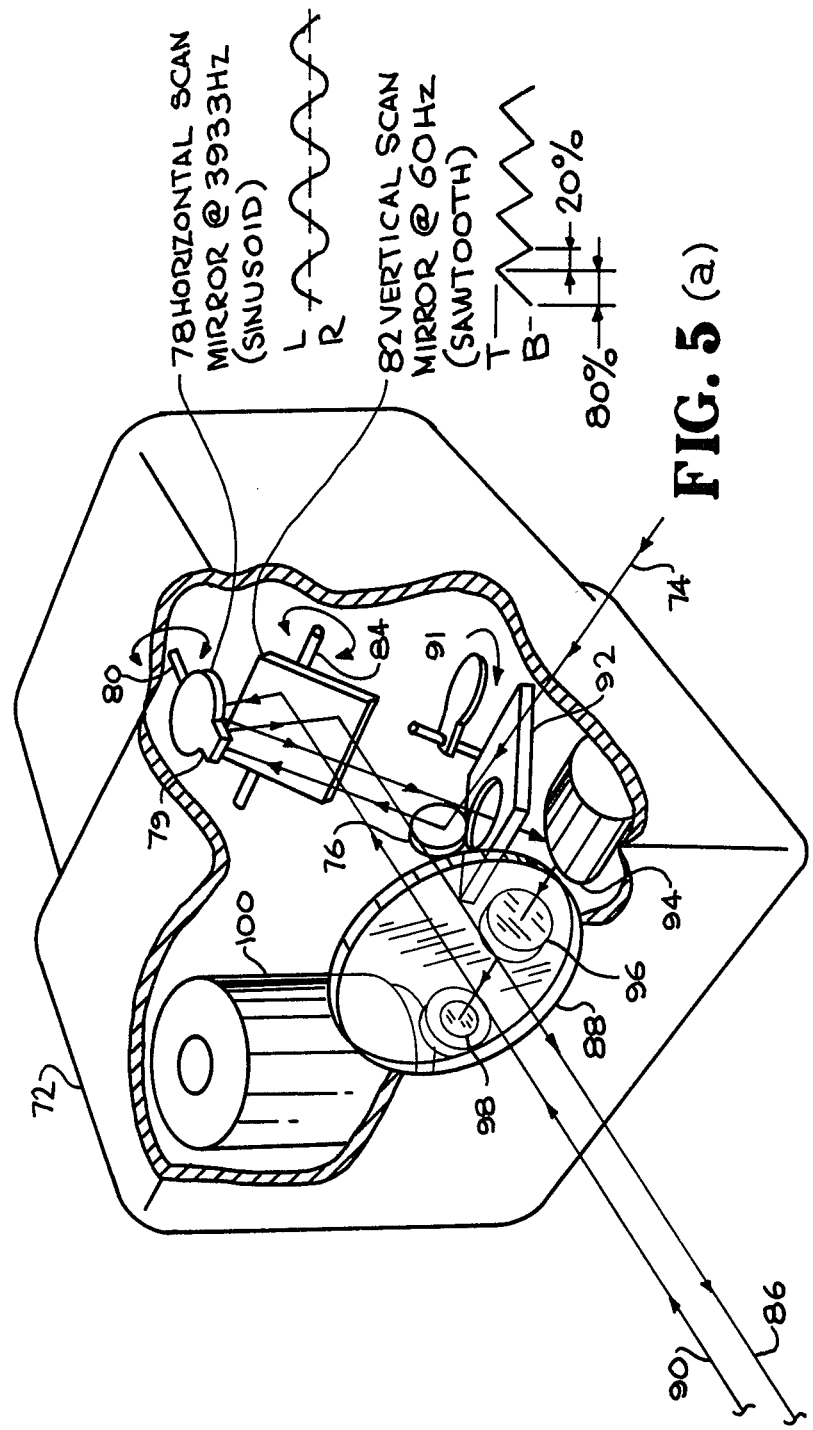

BACKSCATTER ABSORPTION GAS IMAGING SYSTEM

The U.S. Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates to the detection of gas leaks and, more particularly, to a imaging system for producing a video display of leaks of invisible gas.

The transportation and storage of hazardous materials create a significant safety problem. Hazardous gases, in particular toxic or explosive gases, may be released to the environment. Often the gas is colorless and odorless, spreading as an invisible cloud, and creating difficult problems of location, containment and removal.

The natural gas industry, in particular, is concerned about the possible hazards of natural gas leaks at facilities and along transmission lines. Natural gas is a colorless odorless gas made up of 90 percent methane with ethane the next largest component. A natural gas detection system must be capable of leak detection along remotely located gas transmission lines, underground storage facilities, liquified natural gas (LNG) facilities, as well as mains and service lines of local gas distribution systems.

The Liquified Gaseous Fuels (LGF) Spill Effects Program at Lawrence Livermore National Laboratory has been studying the possible hazards associated with large scale spills of hazardous materials, focusing particularly on LNG vapor clouds. A variety of instrumentation has been tested including commercial hydrocarbon detectors, thermal imaging systems, Raman LIDAR systems, and fast response methane and ethane IR gas sensors capable of operating in a fog. Also studied were a commercial IR sensor, an IR helium neon laser absorption detector for methane, and a four band differential radiometer for detection of methane, ethane and propane. All these detection systems have been primarily directed towards the monitoring of large dense clouds of LNG vapors.

A passive infrared (IR) imaging system for use in monitoring LNG vapor cloud dispersion in vapor cloud combustion dynamics has been developed in the LGF program. The passive imaging system is a two wavelength broadband system which, when mounted in a helicopter and using the appropriate choice of interference filters, provides images of the dispersing gas cloud. The system utilizes a passive absorption technique, relying on the thermal radiation from the ground to produce a background image, and the absorption bands of methane, ethane and propane to attenuate the background image when the vapor cloud is present. The system demonstrated the ability to image a LNG vapor cloud from an altitude of 1 kilometer for gas concentrations down to 2-3 percent.

U.S. Pat. No. 3,317,730 discloses a method for determining atmospheric pollution by the detection of backscattered modulated infrared radiation.

U.S. Pat. No. 3,832,548 Wallack shows a general infrared absorption detector in which infrared radiation first passes through a filter means having a plurality of positions for transmitting selected wavelengths, and then passes through a sample cell to a detector.

U.S. Pat. No. 4,204,121 to Milly shows a mobile detector comprising a vertical sampling array for quantifying emission rates from pollution sources.

U.S. Pat. No. 4,264,209 to Brewster shows a system for producing an indication of a concentration of a gas of interest in which the gas is illuminated and the output is filtered alternately with two filters, one at an absorption band of a gas to be detected, the other at a passband outside the absorption band.

U.S. Pat. No. 4,262,199 to Bridges, et al., shows a mobile infrared target detection and recognition system including an assembly of infrared detection elements which scan a field of view to produce a signal representative of the infrared level from point to point.

U.S. Pat. No. 3,829,694 to Goto discloses apparatus for detecting gases or particles using Mie scattering of pulsed light beams to detect resonance absorption.

U.S. Pat. No. 3,517,190 to Astheimer discloses a method for monitoring stack effluent from a remote position by illuminating the effluent across a broad spectral band and detecting the reflected illumination in two spectral regions: one in an absorption band and one outside the absorption band to determine the quantity of absorbing gas from the signal ratio.

Thus, it is desirable to produce a mobile system to locate leaks of hazardous gas, particularly natural gas. A suitable system should not be easily confused by other sources, e.g., hydrocarbons from auto exhaust emissions. An airborne or mobile system is desired. A video imaging system would be highly advantageous since the operator can actually see where the leak is originating, thus eliminating the number of false alarms.

Accordingly, it is an object of the invention to provide a mobile remote detection (surface and/or airborne) system.

It is also an object of the invention to provide a video imaging system to locate hazardous gas leaks.

It is another object of the invention to provide a system which is simple to operate and interpret, e.g., operating in real time.

It is a further object of the invention to provide a detection system with a low false alarm rate.

It is a further object of the invention to provide a rugged, field reliable system.

SUMMARY OF THE INVENTION

The invention is a video imaging system for detecting hazardous gas leaks, particularly for producing a visual display of an invisible gas cloud. The invention is based on the radiation augmentation of the field of view of an imaging device by laser radiation corresponding to an absorption line of the gas species to be detected. The field of view of an imager, e.g., an IR imager, is irradiated by a laser at a wavelength that is absorbed by the gas to be detected. The IR imager receives both backscattered laser light and background radiation from the field of view to produce an image. When no gas is present, the laser light enhances the image. When a detectable gas (absorbing at the laser wavelength) is present, the laser light is attenuated more than the background component, producing a region of contrast or shadow on the image, showing the location of the gas cloud. Instead of irradiating and viewing the whole field at once, a flying spot imaging system can be utilized in which a series of small regions of the field are scanned by the imager and synchronously irradiated by the laser.

DETAILED DESCRIPTION OF THE PREFERRED EMBODIMENT

The invention is an active backscatter absorption method and apparatus for detecting leaks of hazardous gas, particularly invisible gas clouds. The invention comprises a video imaging system with an imager, e.g., an infrared imager, for producing a visual display of the invisible gas leak. The imager field of view is irradiated with a laser at a wavelength which is strongly absorbed by the major components of the hazardous gas. Backscattered laser radiation plus background thermal and/or scattered radiation is detected by the imager to produce a video image. The invention utilizes radiation augmentation of the field of view of an imaging device by laser radiation corresponding to an absorption line of the gas species to be detected. The invention also requires that there be a reflective or scattering background in the field of view and that the laser wavelength correspond to an atmospheric transmission window.

Figure 1:
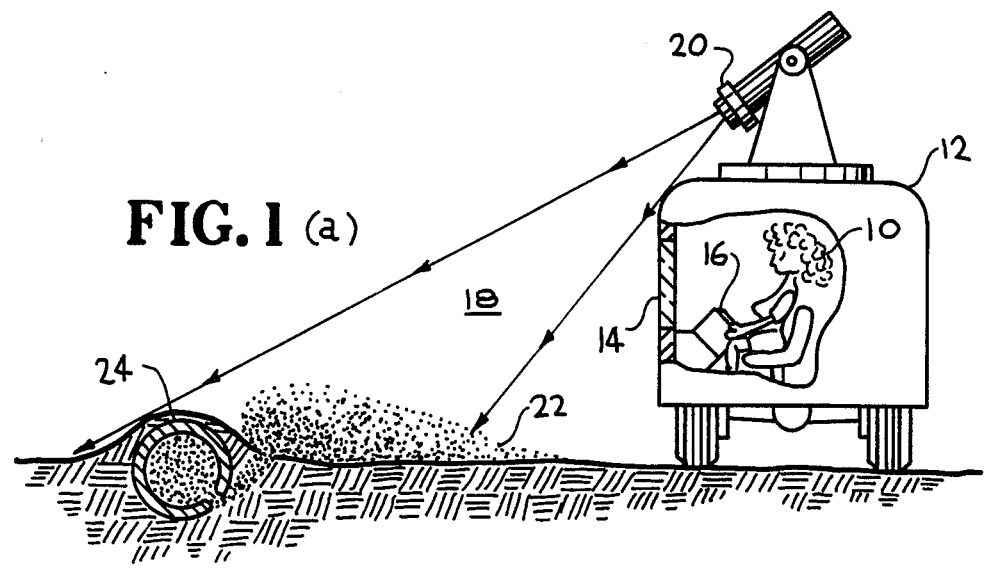
FIG. 1a shows a mobile embodiment of the gas imaging system.
FIG. 1b shows an airborne embodiment of the system.
FIG. 1c shows a fixed/scanning embodiment of the system.
Figure 1:
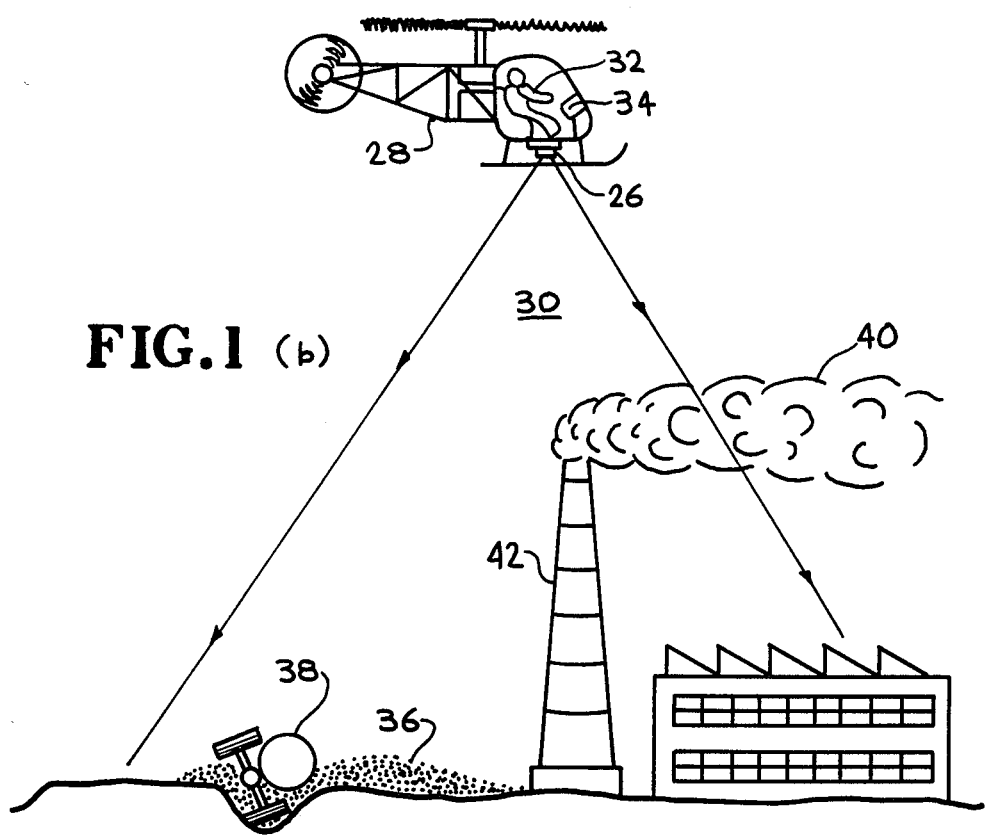
Figure 1:
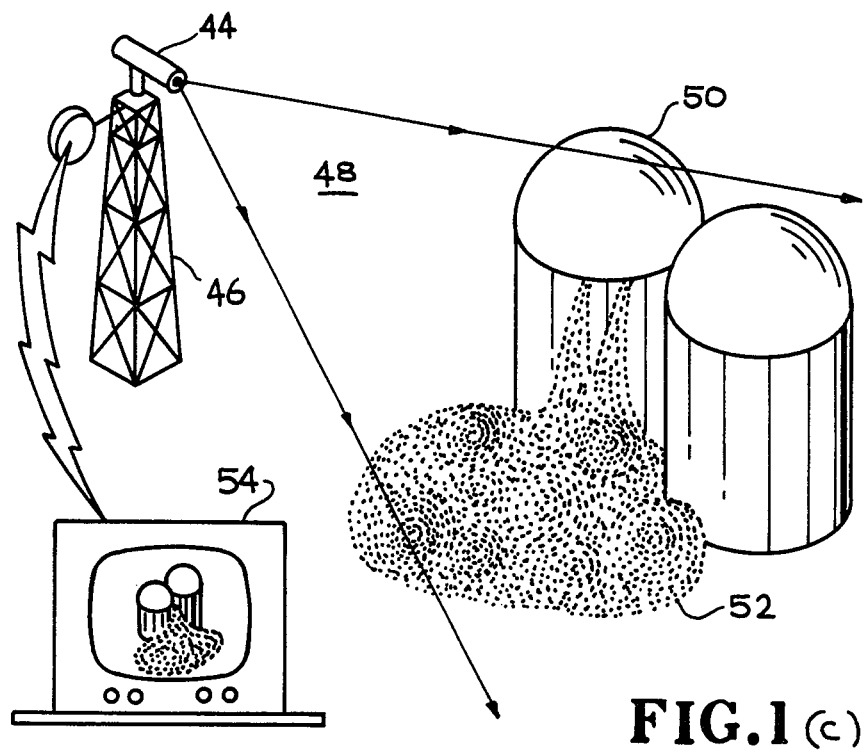

A mobile embodiment of the backscatter absorption gas imaging (BAGI) system for the detection and location of a gas leak is shown in FIG. 1a. An operator 10 in vehicle 12 is able to view the terrain both by eye through window 14 and with the TV monitor 16 which displays the field of view 18 of the backscatter absorption laser/IR detector system 20 which is movably mounted on vehicle 12. In this manner, he is able to see the normally invisible gas cloud 22 which is dispersing from a leak from gas pipe 24. Due to the uniqueness of the laser/gas absorption process, visualization of other gas species (false alarms) is highly unlikely. However, should this occur, the imaging capability allows the operator to see where the gas cloud originates, giving him further information as to its authenticity. Interpretation of the system output is simple and straightforward, and since the data is in a standard TV video format, it can be transmitted "live" to any receiver within range.

An airborne embodiment of the backscatter absorption gas imaging system could be mounted on a helicopter 28, as shown in FIG. 1b, for emergency response to accidental spills of hazardous gases and for routine surveys of gas transmission lines. The laser/detector 26 has a field of view 30 which the operator 32 can display on video monitor 34. Hazardous gas 36 from an accidental spill 38 within the field of view can be detected. Other gas clouds 40 (nonhazardous) from source 42 in the field of view may also be detected, but the operator can easily distinguish the sources.

A stationary embodiment of the gas imaging system, as shown in FIG. 1c, can be mounted on towers for scanning areas where leaks of hazardous gases may occur. The BAGI laser/IR detector 44 is movably mounted on tower 46 to monitor field of view 48 directed at storage tanks 50. Gas leak 52 will be detected and a video image transmitted to command past monitor 54 to provide a video display.

Figure 2:
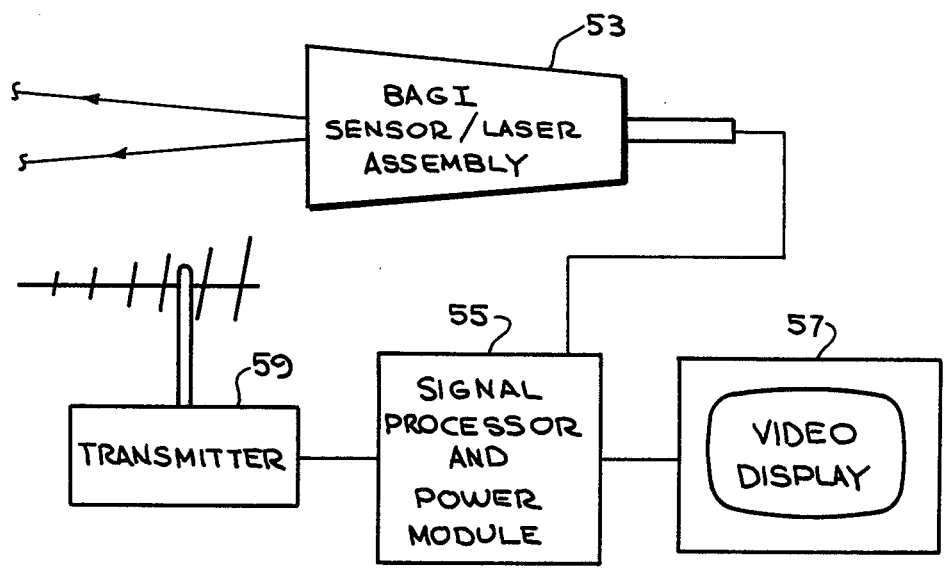
FIG. 2 is a block diagram of the backscatter absorption gas imaging system.

A block diagam showing the major components of the BAGI system is shown in FIG. 2. The sensor/laser unit 53 is controlled by the signal processor and power module 55, and may be located several meters from this module. The signals from the sensor/laser assembly 53 are processed so as to be TV compatible, and can be supplied to either a standard TV video monitor 57 or a TV transmitter 59, or both as shown in FIG. 2.

Figure 3:
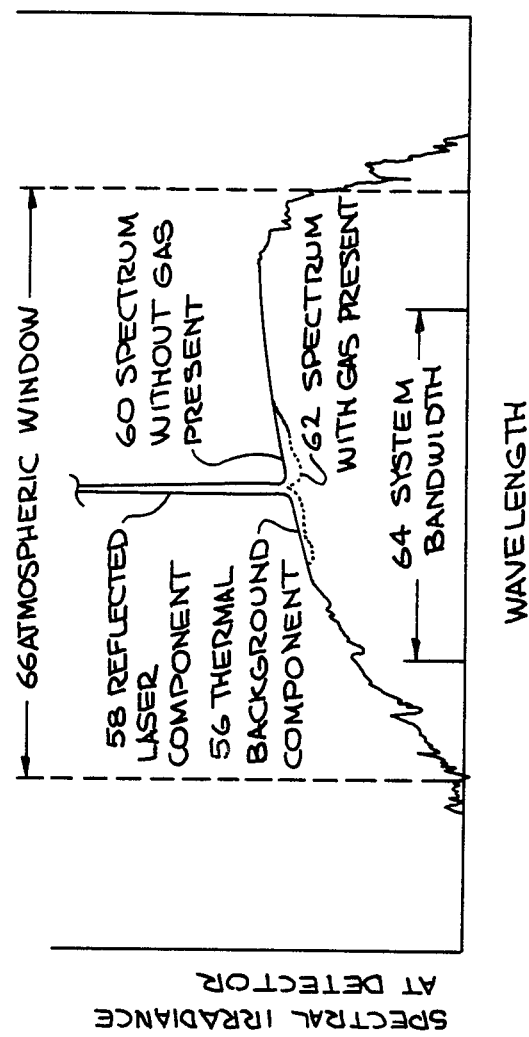
FIG. 3 shows the spectral characteristics of the video imaging system.

The basic principles of the operation of the backscatter absorption gas imaging system are illustrated with reference to FIG. 3, which shows the spectral irradiance at the image system detector. The appropriate laser output beam is made to coincide with the field of view of the imaging system detector. The resulting video image is made up of two components, the thermal and/or ambient background radiation (passive) component 56 emitted by the objects in the field of view plus the reflected laser radiation (active) component 58. In the absence of the hazardous gas, the laser component 58 simply enhances the image of the terrain displayed on the TV monitor, producing the spectrum 60 (solid line FIG. 3). However, when the hazardous gas is present, both the active and passive components of the image are reduced due to molecular absorption, with the laser component 58 being affected the most, to produce the spectrum 62 (dashed line FIG. 3). This difference in the apparent terrain radiance produces an image, or shadow, of the gas cloud on the TV monitor. The higher the gas concentration, the greater is the absorption, and the more apparent the image of the cloud. In this manner, the usually invisible gas cloud becomes "visible" on the video monitor and its size, location, and direction of movement can be determined.

The detection sensitivity of the backscatter absorption gas imaging system is determined primarily by four parameters: image system spectral bandwidth, laser power, terrain reflectivity, and range. The brightness of the image is determined by the integral of the spectral irradiance curve of FIG. 3 over the system spectral bandwidth 64. The largest possible spectral bandwidth will be determined by the natural atmospheric windows 66. Smaller system bandwidths are produced by insertion of optical filters in the imager system optical path. Therefore, for a given laser power, the reflected laser contribution to image brightness increases as the system bandwidth is decreased, and the larger the laser component the more sensitive the technique. If the available laser power were large enough, the system bandwidth could be reduced to the point where essentially all of the image signal was produced by the reflected laser component. Current commercially available lasers are not powerful enough to achieve this smallest system bandwidth limit, hence an optimum bandwidth will exist for a particular laser power. For any particular laser/system bandwidth combination adequate contrast between the terrain image and the gas image will be achieved when the component of the terrain image due to the reflected laser radiation is equal to that produced by the thermal background component. Under these conditions total elimination of the laser component will produce a 50 percent reduction in the cloud image brightness.

The reflectivity of the terrain is also an important contributing factor to the backscatter absorption gas imaging system sensitivity. The fraction of the total laser power illuminating the field of view that actually contributes to the image will depend on the reflectivity of the surfaces. Terrain reflectivities depend on the angle of incidence of the laser radiation, ranging from 0 to 100 percent, with an average value at normal incidence of about 20 percent. Another important factor affecting the sensitivity of the system will be the depth or thickness of the gas cloud. Since the laser component passes through the gas cloud twice, the actual absorption path length is double that of the cloud thickness.

Figure 4A:
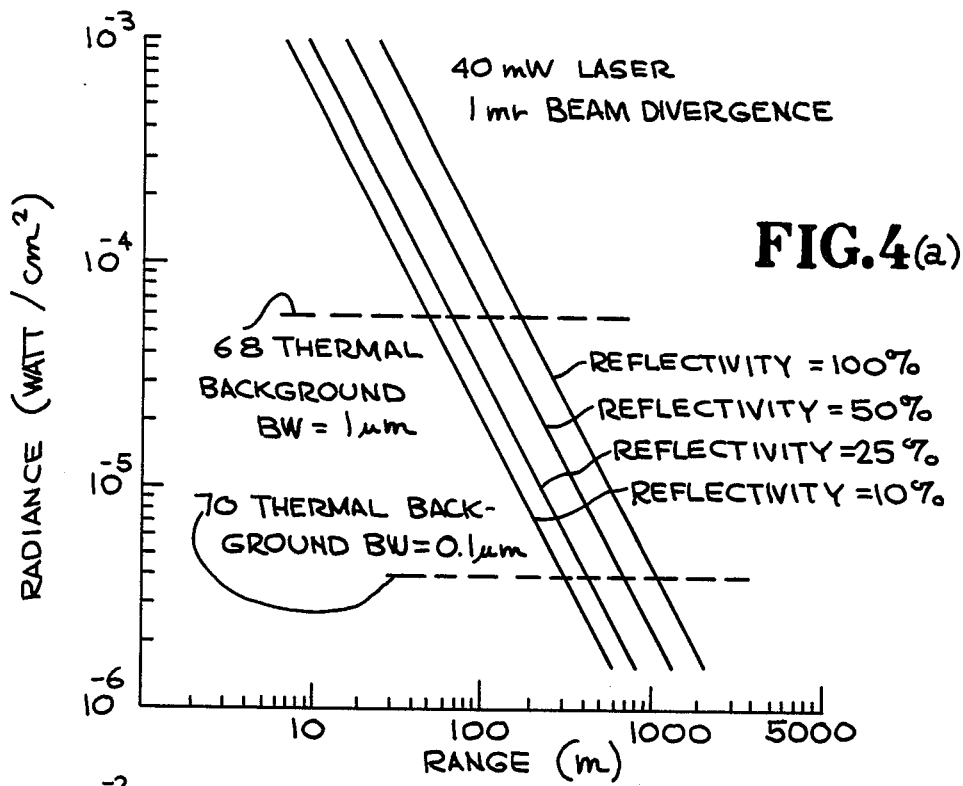
FIGS. 4a and 4b show the range dependence of the video imaging system on spectral bandwidth and terrain reflectivity for two lasers, He-Ne and $CO_2$.
Figure 4B:
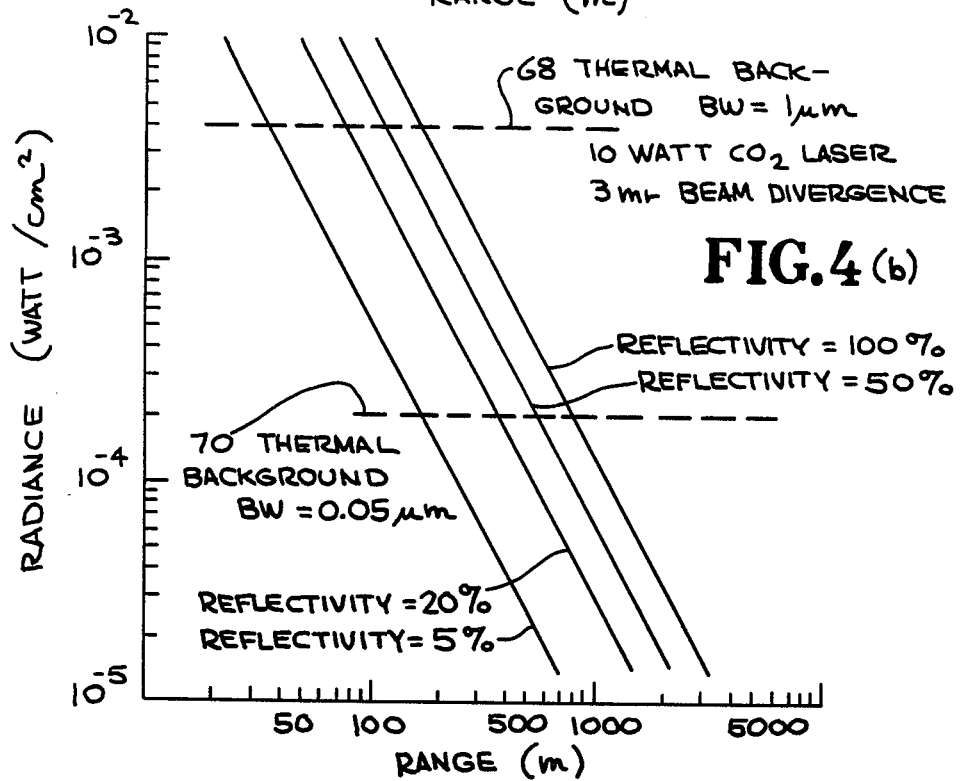

Values of the system bandwidth, laser power, and terrain reflectivity all couple to determine the range of the system. Results of calculations using typical values for these parameters are shown in FIGS. 4a and 4b. FIG. 4a shows the variation of system range with values of terrain reflectivity for a 40 mW IR HeNe laser with a beam divergence of 1 mrad; FIG. 4b shows range for a 10 W $CO_2$ laser with a 3 mr beam divergence. The two system bandwidth background levels 68 and 70 shown were calculated using the blackbody radiance at 300° K., centered at 3.4 $\mu$m in FIG. 4a and 10.5 $\mu$m in FIG. 4b. The optimum system bandwidth will probably lie between these two levels. The intersections of the thermal background levels and reflectivity lines indicate equal contributions of each radiation component to the thermal image and give a reasonable estimate of the range for the system. These calculations do not take into account any absorption of the thermal background radiation by the gas, which would effectively lower both thermal background levels shown in FIGS. 4a and 4b, and improve the range of the system.

The range dependence values of FIGS. 4a and 4b were calculated using a typical laser beam divergence angle (unexpanded). The available beam power of current off-the-shelf lasers of useful dimensions for a backscatter absorption gas imaging system are not adequate to completely illuminate a field-of-view of practical size. Consequently synchronization of the unexpanded laser beam with the horizontal/vertical raster of a "flying spot" (or similar concept) imaging system is required. With the flying spot imaging technique, the video signal is composed of a point-by-point, horizontal and vertical scanning of the field of view. Since the detector only senses a small portion of the field of view at any instant, the laser need only irradiate that same area at the same time. This concept by itself will allow image system enhancement with a minimum of laser power. Thus, in any imaging system which views an irradiated area, the whole area can be systematically irradiated, e.g., by rastering a spot over the area, and radiation from irradiated spots can be synchronously detected, thereby increasing range and sensitivity while keeping down power and size requirements.

Figure 5:
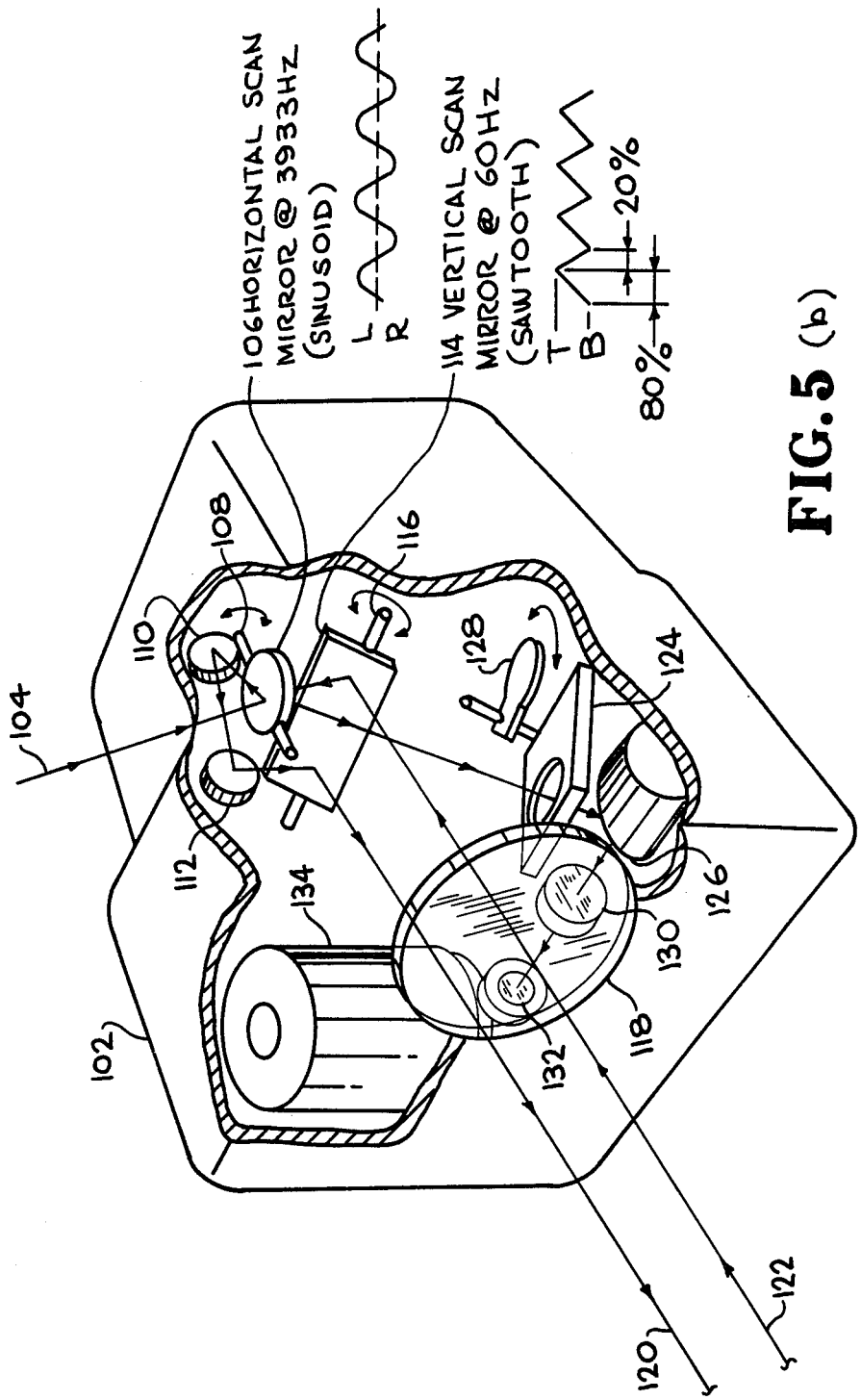
FIG. 5a shows a sectional view of one embodiment of an infrared flying spot imager which sychronizes laser and detector spots.
FIG. 5b is a sectional view of a second embodiment of an infrared flying spot imager which synchronizes laser and detector spot.

Two embodiments of a flying spot imager which would accomplish the synchronization of laser and detector spots are shown in FIGS. 5a and 5b. The imager is a modification of a conventional IR imager, e.g., the Inframetrics, Inc. Model 210 Fast Scan IR Thermal Imager. While a preferred embodiment of the invention utilizes an infrared imager, other imaging systems in the visible or ultraviolet spectrum can be utilized. The invention requires a detector operating over a particular spectrum and a source which provides radiation at a wavelength in that spectrum which is highly absorbed by the species to be detected.

As shown in FIG. 5a the imager 72 has an input laser beam 74 which hits mirror 76 and is directed to horizontal scan mirror 78. The laser beam hits the projection 79 of mirror 78. Horizontal scan mirror 78 is driven sinusoidally about axis 80 at a frequency of 3933 Hz. The laser beam is directed from horizontal scan mirror 78 to vertical scan mirror 82 which is driven about axis 84 by a 60 Hz sawtooth waveform, as shown in FIG. 5a. The laser beam is directed from vertical scan mirror 82 through window 88 forming laser output beam 86 which irradiates the portion of the field of view sensed by the detector 100. The imager 72 coincidentally with the laser output beam 86 receives a light bundle 90 typically $\frac{1}{2}$ inch diameter from the field of view. The light bundle 90 includes both a reflected laser radiation component and a background radiation component. The light bundle 90 passes through window 88 to vertical scan mirror 82 to horizontal scan mirror 78, hitting spots on the mirror adjacent to the input laser beam. The light then passes from mirror 78, past a chopper 91 operating at 60 Hz through filter 92 to folding mirror 94 through focusing lens 96 through Dewar window 98 to detector/Dewar assembly 100, producing an image in the conventional manner. The imager 72 is connected to a signal processing module which generates the video signal necessary to produce the video image.

In the embodiment of FIG. 5b a flying spot imager 102 has a laser input beam 104 which is incident on the backside of the horizontal scan mirror 106 which is driven sinusoidally about axis 108 at a frequency of 3933 Hz. The laser beam is then directed from mirror 106 to mirror 110 to mirror 112 to the vertical scan mirror 114 which is driven about axis 116 by a 60 Hz sawtooth waveform, as shown in FIG. 5b. The laser beam is directed by vertical scan mirror 114 through front window 118 forming laser output beam 120, which irradiates the field of view of the detector. Simultaneously the vertical scan mirror 114 also receives light bundle 122 from the irradiated field of view through front window 118. The light bundle 122 hits a spot on scan mirror 114 adjacent to the input laser beam, and directs the light bundle 122 to the bottom of horizontal scan mirror 106 which directs the light beam through filter 124 to folding mirror 126. The light beam passing from vertical scan mirror 116 to folding mirror 126 ia also chopped by chopper 128 operating at 60 Hz. The chopped light beam from folding mirror 126 passes through focusing lens 130 and through Dewar window 132 to detector/Dewar assembly 134 which produces an image in the conventional manner.

In the embodiment of FIG. 5a the areas of horizontal and vertical scan mirrors 78 and 82 are increased from the conventional design in order to accomodate the laser beam which hits the mirrors at spots adjacent to the light beam received by the imager from the field of view. In the embodiment of FIG. 5b only the area of the vertical scan mirror 114 is increased since both sides of horizontal scan mirror 106 are used, but additional fixed mirrors 110 and 112 are provided. By use of the same mirror scanning system for both the laser and imager detector, synchronization of the two beams is insured. The typical spot divergence angle of the imager is generally greater than typical laser beam divergence angles, thus allowing for complete use of the laser power. Although the spots of the laser beam and light bundle from the field of view are kept separate on the mirrors, this is only to insure that the detector will not be saturated by laser light reflected directly to the detector by defects in the mirror; if this is not a problem, then the spots can coincide on the mirror. Although a preferred embodiment utilizes mirrors to scan the field of view, other imagers utilize rotating polygons or other means which can likewise be used to synchronize the laser and detector according to the invention.

A fundamental requirement for the backscatter absorption gas imaging technique is a laser whose radiation is well absorbed by the species to be detected. Tunable lasers make this requirement theoretically attainable for all gases. However, tunable laser systems are generally expensive, complicated and not currently designed as a field-deployable instruments. Therefore, for practical purposes a reliable mobile backscatter absorption gas imaging system will generally utilize gas or glass lasers. Gas lasers have the necessary wavelength stability, output power, and beam divergence, are reasonably compact and rugged, and can operate in the CW mode. Many hazardous gases are absorbed by existing gas lasers; some of these gases and the corresponding laser, lasing wavelength and respective absorption coefficients are listed in Table 1. The gases include methane ($CH_4$), ethylene ($C_2H_4$), ethane ($C_2H_6$), hydrogen chloride (HCl), ammonia ($NH_3$), nitrous oxide (NO), hydrazine ($N_2H_4$), monomethyl hydrazine (MMH) and unsymmetrical dimethyl hydrazine (UDMH). The calculation of the backscatter absorption gas imaging sensitivity in Table 1 is for the lowest concentration of a gas cloud 5 m thick which is just visible on the TV monitor (greater than 4 percent contrast). The calculation also assumes that the thermal background and reflected laser contributions to the image are equivalent.

TABLE 1

| Gas | Laser | Wavelength (μm) | Absorption Coefficient ($atm^{-1} cm^{-1}$) | Gas Imaging Sensitivity (ppm) |
|---|---|---|---|---|
| $CH_4$ | HeNe | 3.39 | 8.1 | 10 |
| $C_2H_4$ | $CO_2$ | 10.529 | 29.7 | 3 |
| $C_2H_6$ | HeNe | 3.39 | 4.6 | 18 |
| HCl | DF | 3.636 | 5.64 | 15 |
| $NH_3$ | $CO_2$ | 10.331 | 21.9 | 4 |
| NO | CO | 5.176 | 2.75 | 30 |
| $N_2H_4$ | $CO_2$ | 10.441 | 7.56 | 11 |
| MMH | $CO_2$ | 10.334 | 3.48 | 24 |
| UDMH | $CO_2$ | 10.834 | 3.95 | 21 |

Figure 6:
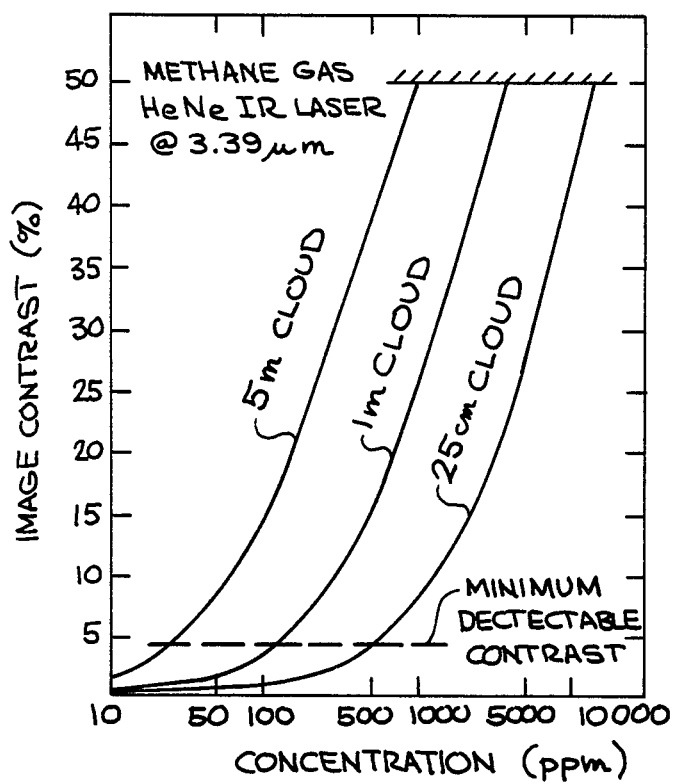
FIG. 6 shows video system sensitivity for various gas cloud conditions, providing image contrast as a function of gas cloud thickness and concentration.

The technique is especially suited for detection of methane and ethane, the major components of natural gas, since the HeNe laser oscillation at 3.3923 μm is strongly absorbed by both of these species. It is also fortunate that the 3–4 μm region is an excellent atmospheric transmission window which is commonly used by most IR imaging systems, and that these IR systems will also permit night time leak visualization. The absorption coefficients for the IR HeNe laser at 3.3923 μm for methane and ethane are 8.1 $atm^{-1} cm^{-1}$ and 4.6 $atm^{-1} cm^{-1}$, respectively. The image contrast as a function of various leak conditions (gas cloud thickness and concentration) is shown in FIG. 6. The curves of FIG. 6 were generated assuming the reflected laser and thermal background components of the image are equal. The minimum detectable contrast for a stationary image is about 4 percent, being somewhat lower for a moving image. The maximum contrast is 50 percent for these calculations and corresponds to the total absorption of the laser component. The estimated minimum sensitivity of the technique ranges from a 200 ppm gas leak, 25 cm thick, to a 10 ppm cloud, 5 m thick.

Changes and modifications of the specifically described embodiments can be carried out without departing from the scope of the invention and is intended to be limited only by the scope of the appended claims.

I claim:

1. Method for detecting the presence of an invisible cloud of gas over a terrain, comprising:
    irradiating an area of the terrain within infrared laser radiation at a single wavelength which is absorbed by the gas and reflected or backscattered by the terrain;
    detecting background infrared radiation from the irradiated area of the terrain;
    detecting backscattered laser radiation from the irradiated area of the terrain;
    producing an image of the terrain from the background radiation;
    enhancing the image of the terrain with the backscattered laser radiation, the irradiating infrared radiation being of sufficient power so that the enhancement of the image by backscattered radiation is about equal in brightness to the image produced by the background radiation;
    producing a region of detectable contrast or shadow over the image of the terrain when the gas is present, said region being primarily due to absorption of the laser light by the gas.

2. Method of claim 1 wherein the steps of detecting radiation from the irradiated area and producing an image are performed by receiving the radiation in an infrared imaging device.

3. Method of claim 1 for detecting natural gas, wherein the step of irradiating the area is performed by irradiating the area with radiation from a helium-neon laser at about 3.39 μm.

4. Method of claim 1 wherein the steps of detecting radiation from the area are performed by systematically scanning the area, and the step of irradiating the area is performed by synchronously irradiating the area being scanned.

5. The method of claim 4 wherein the step of irradiating an area is performed by synchronously scanning the area with unmodulated radiation.

6. The method of claim 1 wherein the step of irradiating an area is performed with unmodulated infrared laser radiation.

7. Method of claim 1 further including the step of displaying the image on a video display device.

8. The method of claim 1 wherein the step of detecting background radiation is performed by detecting radiation at about 3.4 microns wavelength.

9. Apparatus for detecting the presence of an invisible cloud of gas over a terrain comprising:
    an imaging device, the device having a field of view which can be directed at an area of the terrain to detect the presence of the gas therein;
    a single infrared laser operating at a wavelength which is absorbed by the gas to be detected and reflected or backscattered from the terrain, the laser being positioned to irradiate the field of view of the imaging device, the imaging device being responsive to backscattered laser radiation and to background infrared radiation from the terrain in the field of view, the imaging device producing an image of the terrain in the field of view from the backscattered and background radiation if no gas is present, the infrared laser having sufficient power so that the contribution to the image of the terrain from the backscattered radiation is approximately equal to the contribution from the background radiation, the imaging device producing a region of contrast or shadow on the image of the terrain when the gas is present, said region being primarily due to the attenuation of the backscattered laser radiation by the gas; and video display means operatively connected to the imaging device to display an image of the field of view and show the presence of the gas cloud.

10. Apparatus of claim 9 for detecting natural gas, wherein the laser is an IR HeNe laser operating at about 3.39 μm.

11. Apparatus of claim 9 wherein the imaging device is an infrared imager.

12. Apparatus of claim 9 wherein the imaging device sequentially scans a series of narrow regions in the area and the laser synchronously irradiates the regions.

13. Apparatus of claim 12 wherein the imaging device further includes a horizontal scan mirror and a vertical scan mirror, the laser beam being directed to the horizontal scan mirror to the vertical scan mirror to a narrow region of the field of view of the imaging device, radiation from the narrow region being directed to the vertical scan mirror to the horizontal scan mirror to imaging means.

14. Apparatus of claim 13 wherein the horizontal scan mirror is sinusoidally driven about a substantially horizontal plane and the vertical scan mirror is driven by a sawtooth waveform about a substantially vertical plane to raster the laser beam across the field of view and synchronously receive radiation for the irradiated regions in the field of view.

15. The apparatus of claim 12 wherein the laser is an unmodulated laser.

16. The apparatus of claim 9 wherein the laser is a CW laser.

17. The apparatus of claim 9 wherein the laser is an unmodulated laser.

* * * * *